United States Patent
Hu et al.

(10) Patent No.: US 12,201,646 B2
(45) Date of Patent: Jan. 21, 2025

(54) HYDROGEL TABLET FOR RELIEVING ALCOHOLISM AND PROTECTING THE LIVER AS WELL AS PREPARATION PROCESS AND APPLICATION THEREOF

(71) Applicant: GUANGDONG OCEAN UNIVERSITY, Zhanjiang (CN)

(72) Inventors: Zhang Hu, Zhanjiang (CN); Sitong Lu, Zhanjiang (CN); Songzhi Kong, Zhanjiang (CN); Sidong Li, Zhanjiang (CN); Lingyu Zhang, Zhanjiang (CN); Mingneng Liao, Zhanjiang (CN); Chengpeng Li, Zhanjiang (CN); Yu Cheng, Zhanjiang (CN)

(73) Assignee: GUANGDONG OCEAN UNIVERSITY, Zhanjiang (CN)

( * ) Notice: Subject to any disclaimer, the term of this patent is extended or adjusted under 35 U.S.C. 154(b) by 980 days.

(21) Appl. No.: 17/277,673

(22) PCT Filed: Nov. 20, 2020

(86) PCT No.: PCT/CN2020/130265
§ 371 (c)(1),
(2) Date: Mar. 18, 2021

(87) PCT Pub. No.: WO2021/104155
PCT Pub. Date: Jun. 3, 2021

(65) Prior Publication Data
US 2022/0040221 A1    Feb. 10, 2022

(30) Foreign Application Priority Data

Nov. 26, 2019   (CN) .......................... 201911174637.1

(51) Int. Cl.
*A61K 31/722*    (2006.01)
*A61K 9/20*    (2006.01)
(Continued)

(52) U.S. Cl.
CPC .......... *A61K 31/722* (2013.01); *A61K 9/2009* (2013.01); *A61K 9/2013* (2013.01);
(Continued)

(58) Field of Classification Search
CPC .. A61K 31/722; A61K 9/2009; A61K 9/2013; A61K 9/205; A61K 9/2063;
(Continued)

(56) References Cited

U.S. PATENT DOCUMENTS

2008/0131507 A1* 6/2008 Hite ...................... A61K 9/2013
424/464

FOREIGN PATENT DOCUMENTS

WO   WO-2018027083 A1 * 2/2018 ............... A23L 2/66

* cited by examiner

*Primary Examiner* — Blessing M Fubara
(74) *Attorney, Agent, or Firm* — Eschweiler & Potashnik, LLC; Nathan T. Lewis

(57) ABSTRACT

The present disclosure provides a hydrogel tablet for relieving alcoholism and protecting the liver as well as the preparation process and application thereof. The present disclosure firstly provides a composition with the effects of relieving alcoholism and protecting the liver, which comprises the following components on the basis of weight parts: 20~40 parts of chitosan, 25~55 parts of sodium alginate, 3~20 parts of gelatin, 1~10 parts of calcium carbonate and 0.05~0.5 parts of gallic acid. Based on this composition, the present disclosure further provides a hydrogel tablet for relieving alcoholism and protecting the liver. In the present disclosure, chitosan, sodium alginate and calcium carbonate are compounded at an appropriate proportion to form powder particles of chitosan/sodium alginate (shell)-calcium carbonate (core), into which additionally added gelatin and gallic acid to get a product that is the hydrogel tablet.

20 Claims, 5 Drawing Sheets

(51) Int. Cl.
  *A61K 31/734* (2006.01)
  *A61K 33/10* (2006.01)
(52) U.S. Cl.
  CPC ............ *A61K 9/205* (2013.01); *A61K 9/2063* (2013.01); *A61K 9/2072* (2013.01); *A61K 9/2095* (2013.01); *A61K 31/734* (2013.01); *A61K 33/10* (2013.01)
(58) Field of Classification Search
  CPC .. A61K 9/2072; A61K 9/2095; A61K 31/734; A61K 33/10
  See application file for complete search history.

(a) (b)

HYDROGEL TABLET FOR RELIEVING ALCOHOLISM AND PROTECTING THE LIVER AS WELL AS PREPARATION PROCESS AND APPLICATION THEREOF

This application claims priority to Chinese Patent Application No. CN201911174637.1, entitled "HYDROGEL TABLET FOR RELIEVING ALCOHOLISM AND PROTECTING THE LIVER AS WELL AS PREPARATION PROCESS AND APPLICATION THEREOF", filed to China National Intellectual Property Administration on Nov. 26, 2019, the entire contents of which are incorporated herein by reference.

TECHNICAL FIELD

The present disclosure belongs to the technical field of biomedicines, and more specifically pertains to a hydrogel tablet for relieving alcoholism and protecting the liver as well as a preparation process and an application thereof.

BACKGROUND

The number of alcohol-related deaths worldwide each year is about 2.5 million, accounting for 4% of all deaths. Alcohol abuse, especially among young people, has become a major public health problem of the whole society. "Drinking an excessive amount of alcohol harms the body, while drinking a small amount of alcohol keeps the mood light", moderate drinking may have the effects of promoting blood circulation, dredging the channels and collaterals, nourishing Qi to invigorate the stomach, and dispelling dampness and relieving pain. When an excessive amount of ethanol enters the body, beyond the oxidative metabolic capability of the liver, it will accumulate in the body and go into the brain, enabling the brain excited firstly, and then gradually inhibited, which may cause damages to the brain, liver, stomach and kidney.

A normal ethanol metabolic process is: ethanol is absorbed into the bloodstream in the stomach or small intestine and then transferred to the liver, where ethanol is oxidized to acetaldehyde in the presence of ethanol dehydrogenase (ADH), acetaldehyde is then decomposed by acetaldehyde dehydrogenase (ALDH) into acetate, and acetate is finally decomposed into carbon dioxide and water to be passed out of the body. At present, the development of anti-alcoholic medicine products mainly focuses on reducing the absorption of ethanol and promoting the oxidative metabolism of ethanol in the body, but dramatic damages on the stomach and liver caused by the rapid absorption of ethanol are often ignored. The oxidative metabolism of ethanol always induces a reduction of coenzyme NAD in the body, as well as an increase of the enzymatic activity of the liver cytochrome P450. The reduction of coenzyme NAD level inevitably affects the operation of energy supply chain for the tricarboxylic acid cycle of liver cells, resulting in an insufficient energy supply in the cells. However, ethanol metabolites will produce a large amount of free radicals after oxidative metabolism by xanthine oxidase, thereby resulting in lipid peroxidation of liver cell membrane and cell damages. Therefore, after a large amount of alcohol enters the human body, no matter from the perspective of which mechanism, it is difficult to inhibit the damages caused by ethanol and its metabolites.

Stomach absorption of alcohol follows Fick principle. The stronger the wine, the faster it is absorbed. For products intended for relieving alcoholism and inhibiting damages on organs caused by alcohol, the top priority is to reduce alcohol intake into the bloodstream, and all the effects of protecting the liver and nourishing the stomach are based on this. Therefore, it is of a certain market value to prepare a product capable of slowing the quick access of large amounts of alcohol into the liver.

Existing technologies have disclosed various traditional Chinese medicine compositions for relieving alcoholism and protecting the liver. For example, Chinese patent CN201310094706.4 disclosed a health care product for relieving alcoholism and protecting the liver, which comprises acetaldehyde dehydrogenase enzyme preparation, *Pueraria* extract, *Ginseng* extract, *Acanthopanax* extract, *Atractylodes* extract, Wolfberry extract, Turnjujube extract, vitamin B1, vitamin B2, vitamin B6, vitamin C, L-glycine, L-cysteine, and L-alanine, having the effects of alleviating drunkenness and speeding up recover after drinking. Chinese patent CN200910041385.5 disclosed a functional product composition for relieving alcoholism and protecting the liver, which comprises soybean protein, corn protein, *Ginseng, Pueraria* and Turnjujube, having the effects of relieving alcoholism and restoring consciousness. Chinese patent CN201210272537.4 disclosed a preparation for relieving alcoholism and protecting the liver, which is mainly composed of *Pueraria*, Codonopsis, Turnjujube, and Jujube, and its functional factor is oleanolic acid, with the effects of anti-temulence, relieving alcoholism and protecting the liver. However, most of these compositions are used to relieve alcoholism by adding a variety of traditional Chinese medicines, but the components of these traditional Chinese medicines are complicated, the functional components are undefined, they show slow effects and it will take a certain amount of time to take effect, so the alcoholism cannot be relieved in time; moreover, they have a strong taste and smell as well as a poor compliance.

SUMMARY

The primary objective of the present disclosure is to overcome the problem that the existing anti-alcoholic products have the effect of relieving alcoholism but cannot directly reduce the damages to organs caused by the rapid absorption of ethanol as well as to overcome the deficiency of slow effects, thereby to provide a composition with the effects of relieving alcoholism and protecting the liver. The composition with the effects of relieving alcoholism and protecting the liver provided in the present disclosure has simple components, takes effect rapidly, can directly slow the rapid absorption of alcohol, achieves the effect of relieving alcoholism and protecting the liver quickly, and has the advantages of easy administration and no bad odors.

Another objective of the present disclosure is to provide a hydrogel tablet for relieving alcoholism and protecting the liver and a preparation process thereof.

A further objective of the present disclosure is to provide an application of the composition or the hydrogel tablet in preparing preparations for relieving alcoholism and protecting the liver.

The objectives of the present disclosure are achieved through the following technical solutions:

A composition with the effects of relieving alcoholism and protecting the liver comprises the following components on the basis of weight parts: 20~40 parts of chitosan, 25~55 parts of sodium alginate, 3~20 parts of gelatin, 1~10 parts of calcium carbonate and 0.05~0.5 parts of gallic acid.

Wherein, chitosan is a naturally linear polysaccharide, and has unique properties due to the amino groups in its molecular structure. Chitosan can combine with ethanol well by various ways of electrostatic interaction, absorption and encapsulation. It is non-toxic, has good stability, biodegradability and natural bacteriostasis, has extensive sources, and is low in cost.

Alginate is a natural substance extracted from marine algae. It can combine with a substance containing cations (e.g., $Ca^{2+}$) quickly to form a gelatinous substance. Such a gelatinous substance can form a lattice structure through ionic crosslinking, which has good elasticity. However, there are still many problems in the application of a single alginate hydrogel, such as slow biodegradation and poor cell adhesion.

Gelatin contains 20 essential amino acids, which is a product from condensation of various amino acids in certain proportions. It has unique advantages of biodegradability, non-toxicity, biocompatibility and low cost. Fish gelatin has high gel strength, generally higher than those of calfskin gelatin and pigskin gelatin. Fish gelatin has low gelling temperature and melting temperature, being used in the processing of vitamin, pigment as well as pharmaceutical products and other thermally sensitive substances.

In the present disclosure, chitosan, sodium alginate and calcium carbonate are cross-linked in an appropriate proportion to form composite powder particles of chitosan/sodium alginate (shell)-calcium carbonate (core) with core-shell structures. Gelatin is added to form a layer of gelatin membrane, which makes the acid in the stomach less likely to contact calcium carbonate, thus forming flaky gel; when alcohol enters the stomach, the gelatin membrane swells under the mediation of gallic acid, calcium carbonate is decomposed by gastric juice to release calcium ions, the gel is solidified to rapidly encapsulate and adsorb alcohol to form swollen gel, thereby slowing down the sharp absorption of alcohol, thus achieving the effects of relieving alcoholism and protecting the liver; moreover, gelatin can also protect the stability of the hydrogel tablet under the gastric peristalsis, not easily broken and minced; gallic acid is additionally added to enhance the strength of the gelatin membrane in the gastric juice by hydrogen bonding, and also mediate the alcohol solution to penetrate through the gelatin membrane, thus enabling the gel to transform from flaky to swollen; at the same time, gallic acid can adsorb a large amount of alcohol, which further increases the absorption of alcohol by the hydrogel and slows the absorption speed of alcohol.

In a preferable example, the composition with the effects of relieving alcoholism and protecting the liver comprises the following components on the basis of weight parts: 25~35 parts of chitosan, 30~50 parts of sodium alginate, 8~15 parts of gelatin, 3~5 parts of calcium carbonate and 0.1~0.3 parts of gallic acid.

In a preferable example, the composition with the effects of relieving alcoholism and protecting the liver comprises the following components on the basis of weight parts: 30 parts of chitosan, 40 parts of sodium alginate, 11 parts of gelatin, 4 parts of calcium carbonate and 0.2 parts of gallic acid.

In a preferable example, the gelatin is fish gelatin; the fish gelatin is extracted from leftovers of Tilapia, codfish or Tuna. The fish gelatin can be extracted by conventional extraction processes of fish gelatin in the art.

In a preferable example, the calcium carbonate has a particle size of 1000~2500 meshes. If the particle size of calcium carbonate powders is too large (<1000 meshes), then calcium carbonate will directly settle to the bottom of the solution in step S1, thus the uniform encapsulation cannot be achieved; If the particle size of calcium carbonate powders is too small (>2500 meshes), then calcium carbonate will be likely to stick into balls in step S1, resulting in that the prepared powder particles of chitosan/sodium alginate (shell)-calcium carbonate (core) are too large with poor absorption effect of ethanol.

The present disclosure also pertains to a hydrogel tablet for relieving alcoholism and protecting the liver comprising the above composition, or being prepared with the above composition.

In a preferable example, the hydrogel tablet for relieving alcoholism and protecting the liver is prepared by a process comprising the following steps:

S1. According to the weight parts, chitosan is added into an acidic solution to prepare a chitosan solution, the resulting chitosan solution is adjusted to pH=5.5~6.0, into which are added calcium carbonate powders and a sodium alginate solution in order, treated by vortex vibration and then freeze-dried, to get powder particles of chitosan/sodium alginate (shell)-calcium carbonate (core); the powder particles of chitosan/sodium alginate (shell)-calcium carbonate (core) are of a core-shell structure with chitosan/sodium alginate as the shell and with calcium carbonate as the core;

S2. Gelatin is dissolved in hot water to prepare a gelatin solution, into which is added gallic acid with stirring to get a gelatin membrane solution;

S3. The powder particles of chitosan/sodium alginate (shell)-calcium carbonate (core) obtained from S1 are added into the gelatin membrane solution obtained from S2, stirred evenly, freeze-dried, and tableted to get the hydrogel tablet for relieving alcoholism and protecting the liver; During the preparation of the hydrogel tablet for relieving alcoholism and protecting the liver, the concentrations of the chitosan solution, the sodium alginate solution and the gelatin solution have essential impacts on the stability and swelling transforming capacity of the hydrogel tablet, the absorption rate and absorption amount of alcohol as well as the ethanol metabolism in the body. In a preferable example, the concentration of the chitosan solution is preferably 1%~3%, more preferably 1.5%; the concentration of the sodium alginate solution is preferably 0.5%~1.5%, more preferably 1%; the concentration of the gelatin solution is preferably 0.5%~1%, more preferably 0.7%.

In step S1, it is required to control the time for vortex vibration treatment within a certain range. If the time for vortex vibration treatment is too short (<10 min), it would result in uneven encapsulation of calcium carbonate; If the treatment time is too long (>20 min), the macromolecular structure of chitosan/sodium alginate would be affected, such as the interruption of molecular chains, the breakage of intermolecular hydrogen bonds and the like, thus affecting the effects of the prepared encapsulated particles. In a preferable example, the time for vortex vibration treatment in S1 is preferably 10~20 min, more preferably 15 min.

In step S1, it is required to strictly control the pH range of the solution. If the pH of the solution is too small (<5.5), the acidity will be so strong that the subsequently added calcium carbonate may be decomposed directly; If the pH of the solution is too large (>6), chitosan will be precipitated from the solution. In a preferable example, the pH of the solution is preferably adjusted to 5.8 in S1.

The acidic solution in step S1 is an acidic solution commonly used in this field. Any acidic solutions that can dissolve chitosan can be applied in the present disclosure, including inorganic acids and organic acids; the inorganic acids include hydrochloric acid or carbonic acid, and the organic acids include formic acid, acetic acid, oxalic acid, succinic acid, lactic acid, citric acid or pyrogallic acid.

The application of the above composition with the effects of relieving alcoholism and protecting the liver or the above hydrogel tablet for relieving alcoholism and protecting the liver in preparing preparations for relieving alcoholism and protecting the liver is also in the protection scope of the present disclosure.

In addition to being prepared into the above hydrogel tablet for relieving alcoholism and protecting the liver, the above composition with the effects of relieving alcoholism and protecting the liver can also be prepared into tablets, granules, capsules or microsphere dosage forms. Moreover, the above hydrogel tablet for relieving alcoholism and protecting the liver can also be reprocessed into bilayer mini-encapsulated tablets or other pharmaceutically acceptable dosage forms.

Compared with the prior art, the present disclosure has the following beneficial effects:

(1) In the present disclosure, the powder particles of chitosan/sodium alginate (shell)-calcium carbonate (core) are encapsulated with a layer of gelatin membrane, which makes the acid in the stomach less likely to contact calcium carbonate, thus forming flaky gel; when alcohol enters the stomach, the encapsulating layer swells under the mediation of gallic acid, calcium carbonate is decomposed by gastric juice to release calcium ions, the gel is solidified to rapidly encapsulate and adsorb alcohol to form swollen gel, thereby slowing down the sharp absorption of alcohol, thus achieving the effects of relieving alcoholism and protecting the liver;

(2) In the present disclosure, gelatin membrane is used as the encapsulating layer not only to prevent calcium carbonate from being decomposed by the acid in the stomach before alcohol enters the stomach, but also to ensure the stability of the hydrogel tablet under the gastric peristalsis and being not easily broken and minced due to its high gelling strength;

(3) In the present disclosure, gallic acid is added in the gelatin, not only to enhance the strength of the gelatin membrane in the gastric juice by hydrogen-bond interaction, but also to mediate the alcohol solution to penetrate the gelatin membrane, thus making the gel transform from flaky to swollen, and meanwhile the gallic acid can adsorb a large amount of alcohol;

(4) The raw materials used in the present disclosure are easily biodegradable, green and safe; the preparation process is simple and easy to realize industrial production; the provided composition for relieving alcoholism and protecting the liver and the hydrogel tablet for relieving alcoholism and protecting the liver have simple components and take effects quickly, they can directly slow down the sharp absorption of alcohol and rapidly achieve the effect of relieving alcoholism and protecting the liver, as well as have the advantages of easy administration, no bad odors, and good compliance.

DETAILED DESCRIPTION

Figure 1:
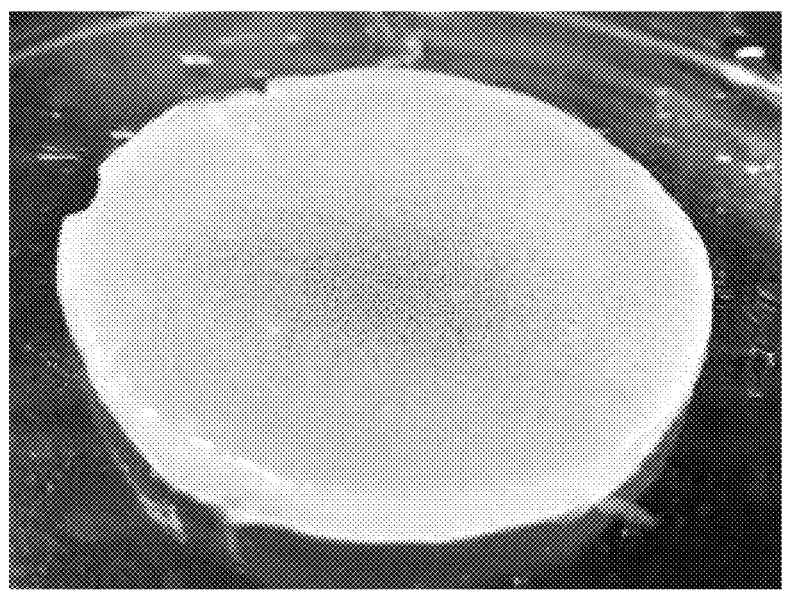
FIG. 1 is a diagram showing the swelling state of the hydrogel tablet for relieving alcoholism and protecting the liver prepared in the present disclosure after adsorbing ethanol.

The present disclosure will be further illustrated below in combination with specific examples, but these examples do not define the present disclosure in any way. The substitution of simple parameters in implementations cannot be detailed in the examples, but the present disclosure is not defined therefore. Any other changes, modifications, substitutions, combinations and simplifications made to the present disclosure without deviating from its spirit and principle are considered as equivalent displacements and all included in the scope of the present disclosure.

Unless specifically illustrated, reagents, processes and equipment used in the present disclosure are conventional reagents, processes and equipment in this technical field.

Unless specifically illustrated, the reagents and materials used in the following examples are commercially available.

Example 1

Preparation of a Hydrogel Tablet for Relieving Alcoholism and Protecting the Liver A hydrogel tablet for relieving alcoholism and protecting the liver comprises the following components on the basis of weight parts: 30 parts of chitosan, 40 parts of sodium alginate, 11 parts of fish gelatin, 4 parts of calcium carbonate and 0.2 parts of gallic acid; the fish gelatin is extracted from leftovers of Tilapia, codfish or Tuna by conventional techniques.

The hydrogel tablet in this example is prepared by a process including the following steps:

S1. According to the weight parts, chitosan is added into an acidic solution to prepare a 1.5% chitosan solution, the resulting chitosan solution is adjusted to pH 5.8, into which are added calcium carbonate powders with particle sizes of 1800 meshes and a sodium alginate solution at a concentration of 1% in order, treated by vortex vibration for 15 minutes, freeze-dried to get powder particles of chitosan/sodium alginate (shell)-calcium carbonate (core);

S2. Gelatin is dissolved in hot water to prepare a 0.7% fish gelatin solution, into which is added gallic acid with stirring to get a fish gelatin membrane solution;

S3. The powder particles of chitosan/sodium alginate (shell)-calcium carbonate (core) obtained from S1 are added into the fish gelatin membrane solution obtained from S2, stirred evenly, freeze-dried, and tableted to get the hydrogel tablet.

Example 2

Preparation of a Hydrogel Tablet for Relieving Alcoholism and Protecting the Liver A hydrogel tablet for relieving alcoholism and protecting the liver comprises the following components on the basis of weight parts: 25 parts of chitosan, 30 parts of sodium alginate, 8 parts of fish gelatin, 3 parts of calcium carbonate and 0.1 parts of gallic acid. The fish gelatin is extracted from leftovers of Tilapia, codfish or Tuna by conventional techniques.

The hydrogel tablet in this example is prepared by a process including the following steps:
- S1. According to the weight parts, chitosan is added into an acidic solution to prepare a 1% chitosan solution, the resulting chitosan solution is adjusted to pH 5.5, into which are added calcium carbonate powders with particle sizes of 1000 meshes and a sodium alginate solution at a concentration of 0.5% in order, treated by vortex vibration for 10 minutes, freeze-dried to get powder particles of chitosan/sodium alginate (shell)-calcium carbonate (core);
- S2. Gelatin is dissolved in hot water to prepare a 0.5% fish gelatin solution, into which is added gallic acid with stirring to get a fish gelatin membrane solution;
- S3. The powder particles of chitosan/sodium alginate (shell)-calcium carbonate (core) obtained from S1 are added into the fish gelatin membrane solution obtained from S2, stirred evenly, freeze-dried, and tableted to get the hydrogel tablet.

Example 3

Preparation of a Hydrogel Tablet for Relieving Alcoholism and Protecting the Liver A hydrogel tablet for relieving alcoholism and protecting the liver comprises the following components on the basis of weight parts: 35 parts of chitosan, 50 parts of sodium alginate, 15 parts of fish gelatin, 5 parts of calcium carbonate and 0.3 parts of gallic acid. The fish gelatin is extracted from leftovers of Tilapia, codfish or Tuna by conventional techniques.

The hydrogel tablet in this example is prepared by a process including the following steps:
- S1. According to the weight parts, chitosan is added into an acidic solution to prepare a 3% chitosan solution, the resulting chitosan solution is adjusted to pH 6.0, into which are added calcium carbonate powders with particle sizes of 2500 meshes and a sodium alginate solution at a concentration of 1.5% in order, treated by vortex vibration for 20 minutes, freeze-dried to get powder particles of chitosan/sodium alginate (shell)-calcium carbonate (core);
- S2. Gelatin is dissolved in hot water to prepare a 1% fish gelatin solution, into which is added gallic acid with stirring to get a fish gelatin membrane solution;
- S3. The powder particles of chitosan/sodium alginate (shell)-calcium carbonate (core) obtained from S1 are added into the gelatin membrane solution obtained from S2, stirred evenly, freeze-dried, and tableted to get the hydrogel tablet.

Example 4

Preparation of a Hydrogel Tablet for Relieving Alcoholism and Protecting the Liver A hydrogel tablet for relieving alcoholism and protecting the liver comprises the following components on the basis of weight parts: 20 parts of chitosan, 25 parts of sodium alginate, 3 parts of gelatin, 1 part of calcium carbonate and 0.05 parts of gallic acid. The fish gelatin is extracted from leftovers of Tilapia, codfish or Tuna by conventional techniques.

The hydrogel tablet in this example is prepared by a process including the following steps:
- S1. According to the weight parts, chitosan is added into an acidic solution to prepare a 1.3% chitosan solution, the resulting chitosan solution is adjusted to pH 5.8, into which are added calcium carbonate powders with particle sizes of 2000 meshes and a sodium alginate solution at a concentration of 0.7% in order, treated by vortex vibration for 20 minutes, freeze-dried to get powder particles of chitosan/sodium alginate (shell)-calcium carbonate (core);
- S2. Gelatin is dissolved in hot water to prepare a 0.7% fish gelatin solution, into which is added gallic acid with stirring to get a fish gelatin membrane solution;
- S3. The powder particles of chitosan/sodium alginate (shell)-calcium carbonate (core) obtained from S1 are added into the fish gelatin membrane solution obtained from S2, stirred evenly, freeze-dried, and tableted to get the hydrogel tablet.

Example 5

Preparation of a Hydrogel Tablet for Relieving Alcoholism and Protecting the Liver A hydrogel tablet for relieving alcoholism and protecting the liver comprises the following components on the basis of weight parts: 40 parts of chitosan, 55 parts of sodium alginate, 20 parts of fish gelatin, 10 parts of calcium carbonate and 0.5 parts of gallic acid. The fish gelatin is extracted from leftovers of Tilapia, codfish or Tuna by conventional techniques.

The hydrogel tablet in this example is prepared by a process including the following steps:
- S1. According to the weight parts, chitosan is added into an acidic solution to prepare a 1.5% chitosan solution, the resulting chitosan solution is adjusted to pH 5.8, into which are added calcium carbonate powders with particle sizes of 2000 meshes and a sodium alginate solution at a concentration of 0.8% in order, treated by vortex vibration for 20 minutes, freeze-dried to get powder particles of chitosan/sodium alginate (shell)-calcium carbonate (core);
- S2. Gelatin is dissolved in hot water to prepare a 1% fish gelatin solution, into which is added gallic acid with stirring to get a fish gelatin membrane solution;
- S3. The powder particles of chitosan/sodium alginate (shell)-calcium carbonate (core) obtained from S1 are added into the fish gelatin membrane solution obtained from S2, stirred evenly, freeze-dried, and tableted to get the hydrogel tablet.

Comparative Example 1

The particle size of calcium carbonate powders is less than 1000 meshes

A hydrogel tablet comprises the following components on the basis of weight parts: 30 parts of chitosan, 40 parts of sodium alginate, 11 parts of fish gelatin, 4 parts of calcium carbonate and 0.2 parts of gallic acid.

Except that the particle sizes of calcium carbonate powders in the comparative example are 800 meshes, the hydrogel tablet in this comparative example is prepared by the same process as that used in Example 1.

Comparative Example 2

Rather than firstly preparing the powder particles of chitosan/sodium alginate (shell)-calcium carbonate (core), the raw materials are blended directly A hydrogel tablet for relieving alcoholism and protecting the liver comprises the following components on the basis of weight parts: 30 parts of chitosan, 40 parts of sodium alginate, 11 parts of fish gelatin, 4 parts of calcium carbonate and 0.2 parts of gallic acid.

The hydrogel tablet in this comparative example is prepared by a process including the following steps:

S1. Calcium carbonate powders, sodium alginate solution, fish gelatin, and gallic acid are directly added into a chitosan solution at a mass concentration of 1.5% in turn and stirred evenly;

S2. The above mixture is freeze-dried, and tableted to get the hydrogel tablet of this comparative example.

Comparative Example 3

Using Porcine Gelatin Instead of Fish Gelatin

A hydrogel tablet comprises the following components on the basis of weight parts: 30 parts of chitosan, 40 parts of sodium alginate, 11 parts of porcine gelatin, 4 parts of calcium carbonate and 0.2 parts of gallic acid.

Except that porcine gelatin is used instead of fish gelatin in this comparative example, the hydrogel tablet in this comparative example is prepared by the same process as that used in Example 1.

Comparative Example 4

No Addition of Gallic Acid

A hydrogel tablet comprises the following components on the basis of weight parts: 25 parts of chitosan, 30 parts of sodium alginate, 8 parts of fish gelatin and 3 parts of calcium carbonate.

Except that gallic acid is not added, the hydrogel tablet in this comparative example is prepared by the same process as that used in Example 1.

Application Example 1

In Vitro Ethanol Absorption Experiment of the Hydrogel Tablet for Relieving Alcoholism and Protecting the Liver 1. Experimental Method Formulation of 5% potassium dichromate: 5 g potassium dichromate (AR) was weighed dissolved in 50 mL water, into which was added 10 mL concentrated sulfuric acid and cooled off, then metered to 100 mL by adding water;

Plotting of ethanol standard curve: 0.25 mL absolute ethanol was accurately weighed and dissolved in distilled water, then metered to 100 mL to get an ethanol solution at a concentration of 0.002 g/mL, which was diluted to solutions at concentrations of $2\times10^{-4}$ g/mL, $4\times10^{-4}$ g/mL, $8\times10^{-4}$ g/mL, $1.2\times10^{-3}$ g/mL and $1.6\times10^{-3}$ g/mL, respectively. Each 0.1 mL of the above solutions was accurately pipetted into colorimetric tubes respectively. Each colorimetric tube was added with 2.0 mL of 5% potassium dichromate solution, adding water to the scale. The colorimetric tubes were heated in a water bath at 100° C. for 10 min, then taken out and cooled with running water for 5 min. The absorbance was determined at a wavelength of 584 nm. An ethanol standard curve was plotted with the absorbance A as the vertical ordinate and with the ethanol concentration as the horizontal ordinate to get a fitting equation: $y=2.6452x-0.0146$, $R^2=0.9995$.

Each 2.0 mL of the hydrogel tablets for relieving alcoholism and protecting the liver prepared in examples 1~5 and the hydrogel tablets prepared in comparative examples 1~4 was respectively mixed evenly with 2.0 mL simulated gastric juice in centrifuge tubes. 1.0 mL absolute ethanol was added, shaken evenly and kept in a water bath for 30 min, and then centrifuged at 4500 r/min in a centrifugal machine for 15 min. The supernatant was poured into a graduated cylinder to measure its volume. 0.1 mL of eluate was accurately pipetted into colorimetric tubes. Each colorimetric tube was added with 2.0 mL of 5% potassium dichromate solution, adding water to the scale. The colorimetric tubes were heated in a water bath at 100° C. for 10 min, then taken out and cooled with running water for 5 min. The absorbance was determined at a wavelength of 584 nm. The ethanol absorption rate was calculated according to the absorbance and the formula below:

$$\text{Ethanol adsorption rate} = \frac{M_0 - M_t}{M_0} \times 100\%,$$

Wherein, Mt is the amount of ethanol deposited, and Mo is the amount of ethanol added.

Each group of samples was determined three times in parallel by repeating the above steps.

The results of in vitro ethanol absorption of the hydrogel tablet for relieving alcoholism and protecting the liver of Example 1 were as shown in FIG. 1.

2. Experimental Results

The results of in vitro ethanol absorption of the hydrogel tablet for relieving alcoholism and protecting the liver as prepared in Example 1 of the present disclosure were as shown in FIG. 1. It is evident from the figure that the hydrogel tablet swells to hydrogel after contacting alcohol to encapsulate a large amount of alcohol, being transparent.

Figure 2:
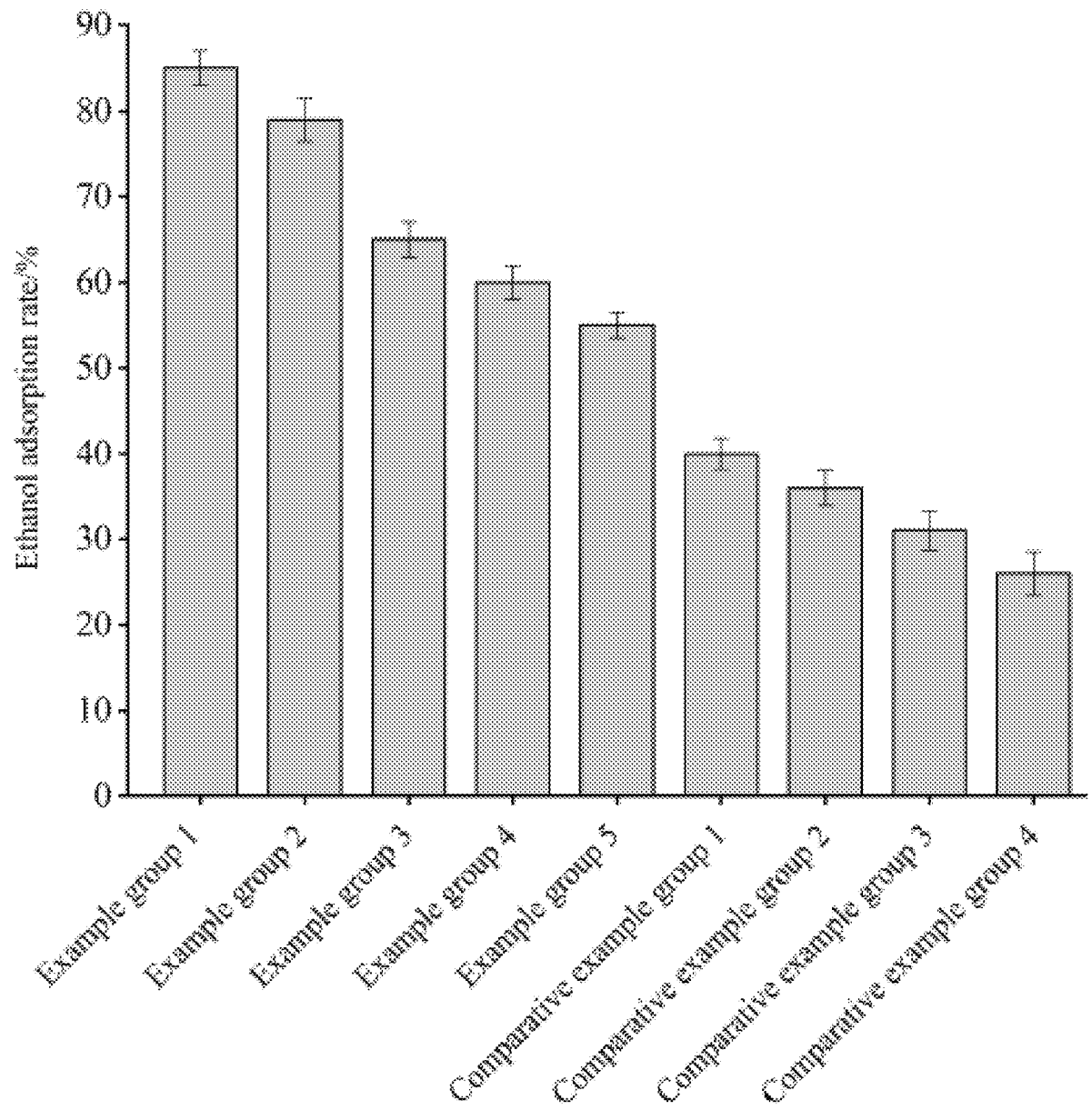
FIG. 2 shows the ethanol absorption rate of the hydrogel tablet for relieving alcoholism and protecting the liver prepared in the present disclosure.

The results of in vitro ethanol absorption of the hydrogel tablets as prepared in the present disclosure are as shown in FIG. 2. As can be seen from the figure, both the hydrogel tablets for relieving alcoholism and protecting the liver prepared in examples 1~5 and the hydrogel tablets of comparative examples 1~4 have obvious absorption effects on ethanol. Wherein, the hydrogel tablets for relieving alcoholism and protecting the liver prepared in examples 1~5 will adsorb more than 50% of alcohol within 30 minutes after alcohol enters the body, which can effectively encapsulate ethanol in the body to slow the rate at which ethanol enters the bloodstream and the liver, thus achieving the effect of relieving alcoholism. In addition, the absorption of the hydrogel tablets for relieving alcoholism and protecting the liver prepared in examples 1~5 on ethanol is significantly stronger than that of the hydrogel tablets of comparative examples 1~4. Wherein, the hydrogel tablet for relieving alcoholism and protecting the liver obtained in Example 1 has the highest ethanol absorption rate, followed by those of Examples 2 and 3, and finally those of Examples 4 and 5.

Application Example 2

Determination on the Anti-Alcoholism Efficacy of the Hydrogel Tablets for Relieving Alcoholism and Protecting the Liver Through establishing anti-alcoholism mouse models, the mice were respectively given the hydrogel tablets for relieving alcoholism and protecting the liver as prepared in examples 1~5 and the hydrogel tablets as prepared in comparative examples 1~4, to determine the anti-alcoholism effects. The statuses of mice were observed, the time of losing righting reflex and the time of restoring righting reflex were recorded, and the anti-alcoholism time, the drunk rate and the death rate were calculated, with the specific experimental method and experimental results as below:

1. Determination of Inebriant Dose

Experimental animals: 172 SPF-grade KM mice, male, body weight 30±2 g, purchased from Guangdong Medical Laboratory Animal Center; they were acclimated for one week before experiments.

Determination of inebriant dose for mice: Mice were randomly divided into 4 groups, 10 mice per group, with fasting and free access to water for 12 h. After then, mice in each group were administrated with different doses (13 mL/kg, 14 mL/kg, 15 mL/kg, 16 mL/kg) of 560 Red Star Erguotou by gavage according to their body weights. The drunken state of mice was observed. The losing of righting reflex in mice was considered as the indicator of drunkenness. The number of intoxicated mice, the anti-alcoholism time and the number of death were recorded to calculate the drunk rate and the death rate of mice.

$$\text{Drunk rate} = \frac{\text{Number of intoxicated mice}}{\text{Number of mice}} \times 100\%;$$

$$\text{Death rate} = \frac{\text{Number of dead mice}}{\text{Number of mice}} \times 100\%;$$

The dose at which the number of intoxicated mice is the maximum and the death rate is the lowest is selected as the inebriant dose of mice.

Figure 3:
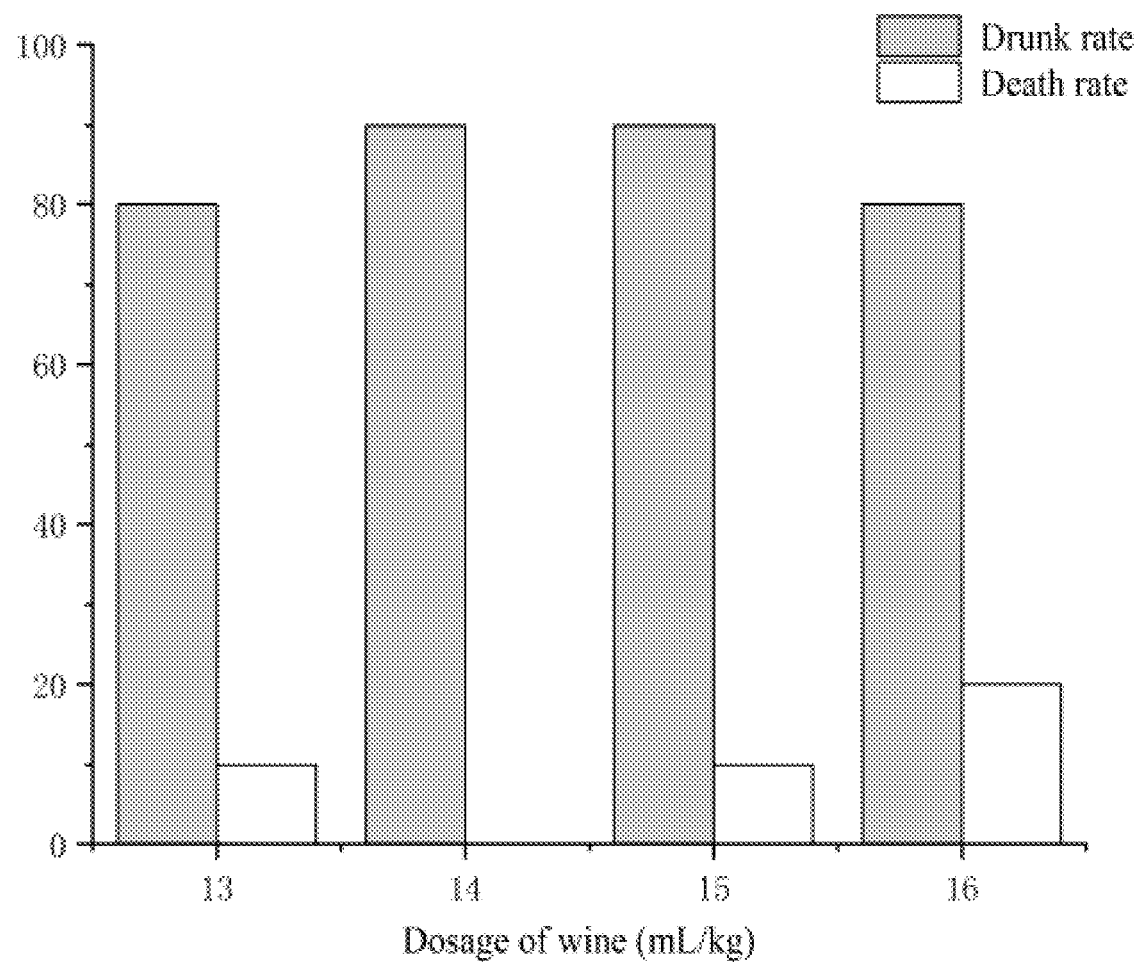
FIG. 3 shows the effects of different dosages of wine on the drunk rate and the death rate of mice.

The results were as shown in FIG. 3. As can be seen from FIG. 3, when the dose of wine for mice was 14 mL/kg, the drunk rate was the highest and the death rate was the lowest. Therefore, 14 mL/kg was selected as the dose of wine by gavage in the anti-alcoholism experiment and the anti-temulence experiment.

2. Anti-Alcoholism Experiment

Experimental animals: 132 mice were randomly divided into 11 groups, with 12 mice per group, including a model control group, a King Drink positive control group, example groups 1~5 and comparative example groups 1~4.

Before the experiment, mice were fasted and had free access to water for 12 h. Then, at a dose of 10 mL/kg, the model control group was given distilled water by gavage; the King Drink positive control group was given King Drink by gavage, the example groups 1~5 were given the hydrogel tablets for relieving alcoholism and protecting the liver as prepared in examples 1~5 by gavage, and the comparative example groups 1~4 were given the hydrogel tablets as prepared in comparative examples 1~4 by gavage. After 30 min, each group was given 560 Red Star Erguotou by gavage respectively at a dose of 14 mL/kg. The losing of righting reflex in mice was considered as the indicator of drunkenness. The time of losing righting reflex and the time of restoring righting reflex were recorded to calculate the anti-alcoholism time (the time of restoring righting reflex—the anti-alcoholism time), the drunk rate and the death rate.

3. Experimental Results

Figure 4:
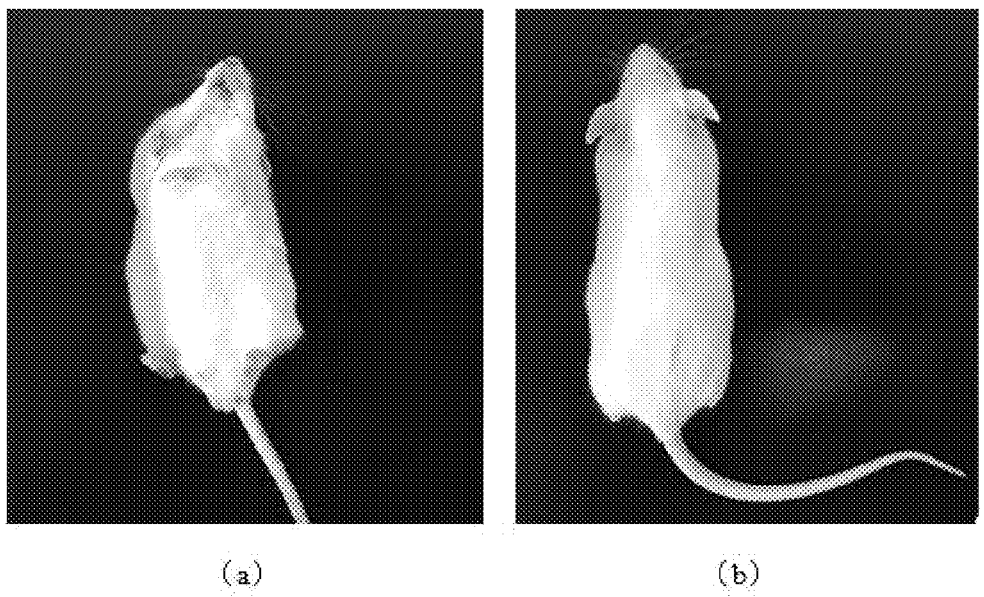
FIG. 4 are diagrams showing the status of mice after intragastric administration of alcohol, wherein, (a) shows the status of mice that have not been administrated with the hydrogel tablet for relieving alcoholism and protecting the liver prepared in the present disclosure, (b) shows the status of mice that have been administrated with the hydrogel tablet for relieving alcoholism and protecting the liver prepared in the present disclosure.

The anti-alcoholism effect of mice which had been administrated with the hydrogel tablet for relieving alcoholism and protecting the liver as prepared in Example 1 of the present disclosure was shown in FIG. 4. As can be seen from FIG. 4, mice which had been administrated with the hydrogel tablet for relieving alcoholism and protecting the liver had smooth hair and sensitive responses, and the righting reflex did not disappear.

The results of the anti-alcoholism time, the drunk rate and the death rate for mice were as shown in Table 1. As can be seen from Table 1, compared with the King Drink positive group and the control groups, the drunk rate, the death rate, and the anti-alcoholism time in Example groups 1~5 were all lower than those in the King Drink positive control group and comparative examples 1~4, and the difference was very significant ($p<0.01$). Wherein, the hydrogel tablet for relieving alcoholism and protecting the liver obtained in Example 1 caused the shortest anti-alcoholism time and relieved the alcoholism most rapidly, indicating that the hydrogel tablet for relieving alcoholism and protecting the liver of the present disclosure can effectively adsorb ethanol in the body, thus achieving the effect of relieving alcoholism. However, for comparative examples 1~4 compared with the positive control group, except for comparative example 1, there were no differences among comparative example groups 2~4 only in terms of the drunk rate and the death rate; but from the view of the anti-alcoholism time, comparative examples 1~4 were higher than the positive control group, with significant differences.

TABLE 1

Results of anti-alcoholism experiment (n = 12)

| Groups | Drunk rate/% | Death rate/% | Anti-alcoholism time (min) |
| --- | --- | --- | --- |
| Model control group | 83 | 17 | 478.50 ± 23.30 |
| Positive control group | 67 | 17 | 370.56 ± 30.50 |
| Example group 1 | 33 | 0 | 220.39 ± 26.50** |
| Example group 2 | 33 | 0 | 250.89 ± 10.59** |
| Example group 3 | 33 | 0 | 269.23 ± 20.89** |
| Example group 4 | 33 | 0 | 275.56 ± 15.69** |
| Example group 5 | 33 | 0 | 277.47 ± 13.73** |
| Comparative example group 1 | 50 | 0 | 390.29 ± 21.63* |
| Comparative example group 2 | 67 | 17 | 410.32 ± 12.56** |
| Comparative example group 3 | 67 | 17 | 425.60 ± 12.23** |
| Comparative example group 4 | 67 | 17 | 440.56 ± 25.55** |

Note:
Compared with the positive control group, $*p < 0.05$, $**p < 0.01$.

Application Example 3

Determination on the Anti-Temulence Efficacy of the Hydrogel Tablet for Relieving Alcoholism and Protecting the Liver Through establishing anti-temulence mouse models, the mice were respectively given the hydrogel tablets for relieving alcoholism and protecting the liver as prepared in examples 1~5 and the hydrogel tablets as prepared in comparative examples 1~4, to determine the anti-temulence effects. The statuses of mice were observed, the time of losing righting reflex and the time of restoring righting reflex were recorded, and the changes in the drunk time, the drunk rate and the death rate were calculated, with the specific experimental method and experimental results as below:

1. Experimental Method

Experimental animals: 132 mice were randomly divided into 11 groups, with 12 mice per group, including a model control group, a King Drink positive control group, example groups 1~5 and comparative example groups 1~4.

Before the experiment, mice were firstly fasted and had free access to water for 12 h. Then, each group was given 560 Red Star Erguotou by gavage respectively at a dose of 14 mL/kg. After 5 min, the King Drink positive control group, the example groups 1~5 and the comparative example groups 1~4 were respectively given 10 mL/kg of corresponding medicines at corresponding concentrations, and the model group was given an equal volume of distilled water. The losing of righting reflex in mice was considered as the indicator of drunkenness. The time of losing righting reflex was recorded to calculate the drunk time (the time of losing righting reflex—the drunk time).

2. Experimental Results

The drunk rate, the death rate and the drunk time for mice were as shown in Table 2. As can be seen from Table 2, compared with the positive control group, the drunk times in example groups 1~5 and comparative example groups 1~4 were all greater than that in the positive control group, especially example groups 1~5 had very significant differences ($p<0.01$). However, from the view of the drunk rate and the death rate, example groups 1~5 were all lower than that of the positive control group. For comparative example groups 1~4, except for the comparative example 1, the remaining comparative example groups were the same as or even higher than the positive control group, indicating that changing the composition or preparation process of the hydrogel tablets has significant effects on the anti-temulence efficacy.

TABLE 2

Results of anti-temulence experiments (n = 12)

| Groups | Drunk rate/% | Death rate/% | Drunk time (min) |
|---|---|---|---|
| Model control group | 67 | 33 | 36.23 ± 9.18** |
| Positive control group | 67 | 17 | 79.55 ± 10.36 |
| Example group 1 | 33 | 0 | 171.69 ± 15.56** |
| Example group 2 | 33 | 0 | 156.35 ± 16.69** |
| Example group 3 | 33 | 0 | 130.23 ± 12.32** |
| Example group 4 | 33 | 0 | 109.39 ± 13.36** |
| Example group 5 | 33 | 0 | 103.55 ± 12.59** |
| Comparative example group 1 | 50 | 0 | 97.46 ± 11.58** |
| Comparative example group 2 | 67 | 17 | 89.98 ± 11.99* |
| Comparative example group 3 | 67 | 33 | 85.78 ± 9.89 |
| Comparative example group 4 | 67 | 33 | 83.65 ± 10.23 |

Note:
Compared with the positive control group, *$p < 0.05$, **$p < 0.01$.

It can be seen from the combination of Table 1 and Table 2 that, the time of restoring righting reflex (anti-alcoholism time) was significantly shortened and the time of losing righting reflex (the drunk time) was significantly prolonged in example groups 1~5, wherein the hydrogel tablet for relieving alcoholism and protecting the liver obtained in Example 1 has the best anti-alcoholism effect.

Application Example 4

In Vivo Ethanol Metabolism Experiment of the Hydrogel Tablet for Relieving Alcoholism and Protecting the Liver 1. Experimental Method The anti-alcoholism and anti-temulence effects in mice were further verified by determining the ethanol contents in the blood of mice after drinking at different time points.

For each time point, 132 mice were randomly divided into 11 groups, with 12 mice per group, including a model control group, a King Drink positive control group, example groups 1~5 and comparative example groups 1~4.

Before the experiment, mice were fasted and had free access to water for 12 h. Then, at a dose of 10 mL/kg, the model control group was given distilled water by gavage; the King Drink positive control group was given King Drink by gavage, and the example groups 1~5 and the comparative example groups 1~4 were respectively given corresponding medicines by gavage. After 30 min, each group was given 560 Red Star Erguotou by gavage respectively at a dose of 14 mL/kg. After a certain time, blood was sampled from the eyeballs of mice, and the content of ethanol in the serum was determined by gas chromatography.

2. Experimental Results

Figure 5:
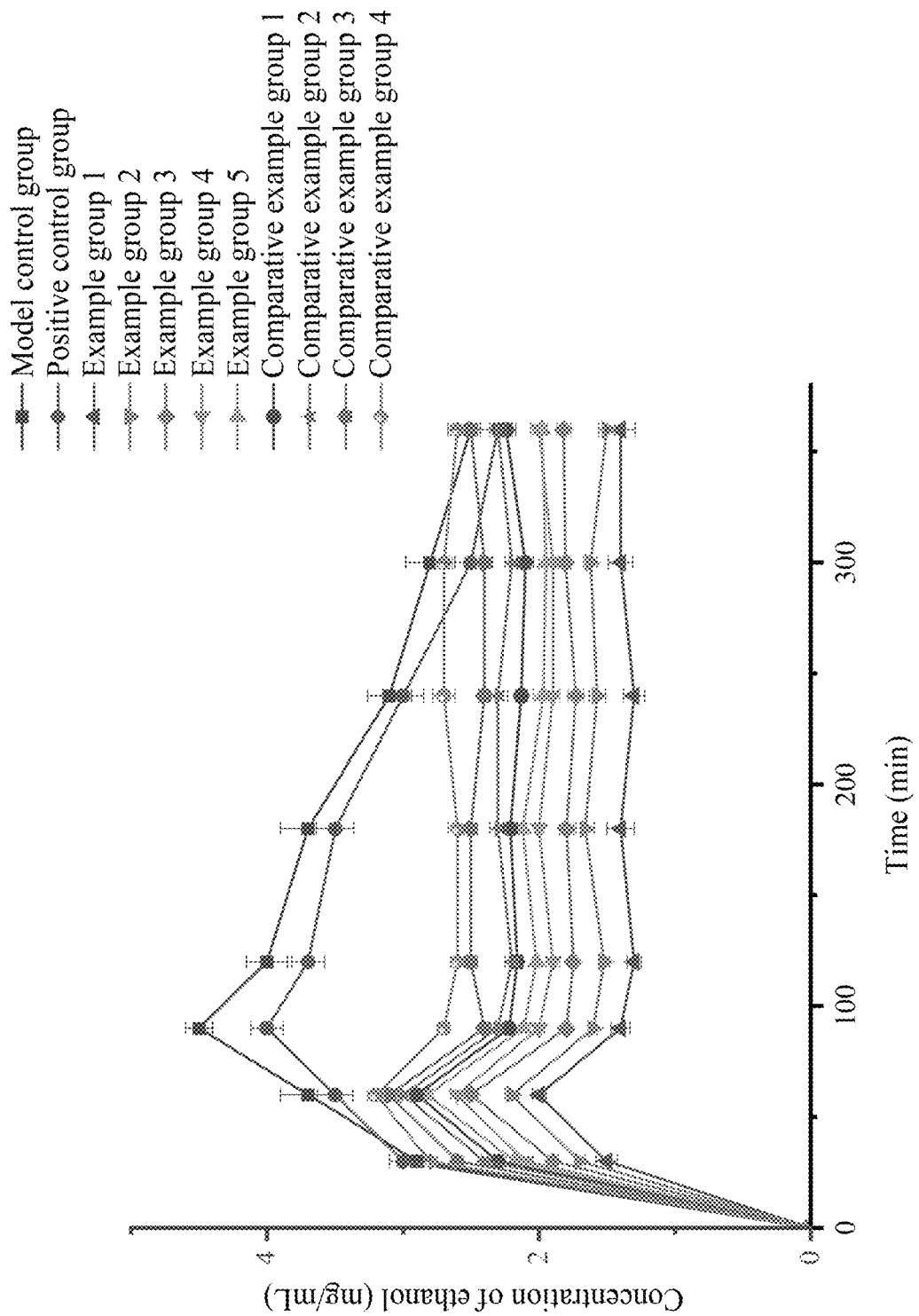
FIG. 5 shows the results of ethanol metabolism in vivo in mice after being administrated with the hydrogel tablet for relieving alcoholism and protecting the liver prepared in the present disclosure.

In vivo ethanol metabolism results of the hydrogel tablet for relieving alcoholism and protecting the liver were as shown in FIG. 5. As can be seen from FIG. 5, the ethanol contents in the blood of the model control group and the positive control group increased firstly and then decreased, reaching a maximum at 90 min, which was beyond the enzymolysis capacity of ethanol dehydrogenase and acetaldehyde dehydrogenase in the body, and the ethanol contents in the blood were high. Compared with the positive control group, example groups 1~5 and comparative examples 1~4 all can effectively reduce the ethanol content in the blood, delay the entry of ethanol into the blood stream, slowly release ethanol at 60 min after there were different extent of release, maintain the ethanol content in the blood and decompose ethanol under the activity of ethanol dehydrogenase and acetaldehyde dehydrogenase in vivo. The effects of the comparative example groups 1~4 were significantly weaker than those of example groups 1~5; and the hydrogel tablet for relieving alcoholism and protecting the liver obtained in Example 1 resulted in the lowest ethanol content in the blood.

Application Example 5

Determination on the Liver-Protection Efficacy of the Hydrogel Tablet for Relieving Alcoholism and Protecting the Liver The elevated activities of ALT and AST are specific indicators of impaired liver function, and the numerical values of ALT and AST objectively reflect the extent of liver cell damages.

1. Experimental Method

Experimental animals: 132 mice were randomly divided into 11 groups, with 12 mice per group, including a model control group, a King Drink positive control group, example groups 1~5 and comparative example groups 1~4.

Mice of each group were given 56° Red Star Erguotou white wine by gavage every day, and 1 h later, they were given the corresponding medicine solutions by gavage respectively at a dose of 10 mL/kg; the model group was given distilled water by gavage continuously for 10 weeks; at the end of the last gavage, mice were fasted and had free access to water for 12 h, and then samples were collected to determine the contents of alanine transaminase (ALT) and aspartate transaminase (AST) in the serum of mice by a velocity process with a fully automatic biochemical analyzer.

2. Experimental Results

The liver protection effects on mice which have been administrated with the hydrogel tablet for relieving alcoholism and protecting the liver were as shown in Table 3. As can be seen from Table 3, compared with the model control group, the contents of ALT and AST in the sera of mice in example groups 1~5 were significantly lower than that of the positive control group ($p<0.01$), indicating that the hydrogel tablet for relieving alcoholism and protecting the liver prepared in the present disclosure can inhibit ethanol from entering the liver, thus causing less damages to liver cells. Wherein, the concentrations of ALT and AST in the serum using the hydrogel tablet for relieving alcoholism and protecting the liver obtained in Example 1 were the lowest; while the contents of ALT and AST in the sera of mice of the comparative example groups 1~4 were higher than that of the positive control group, indicating that changing the composition and preparation process can significantly affect the anti-alcoholic and liver protection effects of the hydrogel tablet.

TABLE 3

Concentrations of ALT and AST in sera of each group of mice (U/L)

| Groups | ALT(U/L) | AST(U/L) |
| --- | --- | --- |
| Model control group | 38.00 ± 2.00 | 157.33 ± 8.68 |
| Positive control group | 34.67 ± 1.56 | 121.67 ± 7.57 |
| Example group 1 | 26.33 ± 3.06** | 101.67 ± 8.77** |
| Example group 2 | 28.06 ± 2.25** | 103.33 ± 9.29** |
| Example group 3 | 19.15 ± 1.07** | 104.12 ± 6.01** |
| Example group 4 | 19.87 ± 2.08** | 107.05 ± 6.89** |
| Example group 5 | 30.13 ± 1.05** | 108.51 ± 7.36** |
| Comparative example group 1 | 35.09 ± 1.58 | 123.67 ± 11.15 |
| Comparative example group 2 | 36.33 ± 1.53 | 129.33 ± 9.01 |
| Comparative example group 3 | 36.84 ± 2.01 | 132.00 ± 8.19 |
| Comparative example group 4 | 37.03 ± 2.52 | 137.67 ± 6.14 |

Note:
Compared with the positive control group, *$p < 0.05$, **$p < 0.01$.

Example 6

A composition with the effects of relieving alcoholism and protecting the liver as well as conventional tablets containing the composition The composition with the effects of relieving alcoholism and protecting the liver comprises the following components on the basis of weight parts: 20 parts of chitosan, 25 parts of sodium alginate, 3 parts of gelatin, 1 part of calcium carbonate and 0.05 parts of gallic acid.

Conventional tablets containing components of the following mass fractions were manufactured by conventional means:
5 wt % of the composition with the effects of relieving alcoholism and protecting the liver of this example;
75 wt % of corn starch;
19 wt % of talc powder; and
1 wt % of magnesium stearate.

Example 7

A composition with the effects of relieving alcoholism and protecting the liver as well as granules containing the composition The composition with the effects of relieving alcoholism and protecting the liver comprises the following components on the basis of weight parts: 40 parts of chitosan, 55 parts of sodium alginate, 20 parts of gelatin, 10 parts of calcium carbonate and 0.5 parts of gallic acid.

Granules containing components of the following mass fractions were manufactured by conventional means:
15 wt % of the composition with the effects of relieving alcoholism and protecting the liver of this Example;
74 wt % of corn starch;
10 wt % of sodium methyl cellulose; and
1 wt % of magnesium stearate.

Example 8

A composition with the effects of relieving alcoholism and protecting the liver as well as capsules containing the composition The composition with the effects of relieving alcoholism and protecting the liver comprises the following components on the basis of weight parts: 25 parts of chitosan, 30 parts of sodium alginate, 8 parts of gelatin, 3 parts of calcium carbonate and 0.1 parts of gallic acid.

Capsules containing the following components were manufactured by conventional means:
50 wt % of the composition of this example;
20.0 wt % of lactose;
20.0 wt % of corn starch; and
10.0 wt % of talc powder.

Example 9

A composition with the effects of relieving alcoholism and protecting the liver as well as microspheres containing the composition The composition with the effects of relieving alcoholism and protecting the liver comprises the following components on the basis of weight parts: 25~35 parts of chitosan, 30~50 parts of sodium alginate, 8~15 parts of gelatin, 3~5 parts of calcium carbonate and 0.1~0.3 parts of gallic acid.

Microspheres containing the following components were manufactured by conventional means:
95 wt % of the composition of this example;
2.5 wt % of sodium carboxymethylcellulose; and
2.5 wt % of hyaluronic acid.

Example 10

A composition with the effects of relieving alcoholism and protecting the liver as well as microspheres containing the composition The composition with the effects of relieving alcoholism and protecting the liver comprises the following components on the basis of weight parts: 30 parts of chitosan, 40 parts of sodium alginate, 11 parts of gelatin, 4 parts of calcium carbonate and 0.2 parts of gallic acid.

Microspheres containing the following components were manufactured by conventional means:
80 wt % of the composition of this example;
10 wt % of sodium carboxymethylcellulose; and
10 wt % of hyaluronic acid.

The applicant claims that, the foregoing detailed descriptions are the preferred examples for ease of understanding the present disclosure, but the present disclosure is not confined to the above examples. That is, it does not mean that the present disclosure must rely on the above examples to be implemented. It should be clear to technical personnel in the art that any improvements to the present disclosure, equivalent replacements of raw materials used in the present disclosure and the addition of auxiliary components as well as the choice of specific means all fall within the protection scope and the disclosure scope of the present disclosure.

What is claimed is:

1. A composition with the effects of relieving alcoholism and protecting the liver, comprising a powder particle including the following components on the basis of weight parts: 20-40 parts of chitosan, 25-55 parts of sodium alginate, 3-20 parts of gelatin, 1-10 parts of calcium carbonate and 0.05-0.5 parts of gallic acid;
wherein the powder particle comprises chitosan/sodium alginate shell-calcium carbonate core of a core-shell structure encapsulated with a layer gelatin membrane, wherein the chitosan/sodium alginate forms the shell and the calcium carbonate forms the core.

2. The composition according to claim 1, wherein, it comprises the following components on the basis of weight parts: 25-35 parts of chitosan, 30-50 parts of sodium alginate, 8-15 parts of gelatin, 3-5 parts of calcium carbonate and 0.1-0.3 parts of gallic acid.

3. The composition according to claim 2, wherein, it comprises the following components on the basis of weight parts: 30 parts of chitosan, 40 parts of sodium alginate, 11 parts of gelatin, 4 parts of calcium carbonate and 0.2 parts of gallic acid.

4. The composition according to claim 1, wherein, the gelatin is fish gelatin; the fish gelatin is extracted from leftovers of Tilapia, codfish or Tuna.

5. The composition according to claim 1, wherein, the calcium carbonate has a particle size of 1000-2500 meshes.

6. The composition according to claim 1, having the effects of relieving alcoholism and protecting the liver.

7. The composition according to claim 6, wherein, the composition is in the form of preparations comprising tablets, granules, capsules or microspheres.

8. The composition according to claim 7, wherein, the preparations are tablets, the tablets comprise components of the following mass fractions: 5 wt % of the composition with the effects of relieving alcoholism and protecting the liver, 75 wt % of corn starch, 19 wt % of talc powder, and 1 wt % of magnesium stearate;
wherein by mass fractions, the composition with the effects of relieving alcoholism and protecting the liver comprises 20 parts of chitosan, 25 parts of sodium alginate, 3 parts of gelatin, 1 part of calcium carbonate and 0.05 parts of gallic acid.

9. The composition according to claim 7, wherein, the preparations are granules, the granules comprise components of the following mass fractions: 15 wt % of the composition with the effects of relieving alcoholism and protecting the liver, 74 wt % of corn starch, 10 wt % of sodium methyl cellulose, and 1 wt % of magnesium stearate;
wherein by mass fractions, the composition with the effects of relieving alcoholism and protecting the liver comprises 40 parts of chitosan, 55 parts of sodium alginate, 20 parts of gelatin, 10 parts of calcium carbonate and 0.5 parts of gallic acid.

10. The composition according to claim 7, wherein, the preparations are capsules, the capsules comprise components of the following mass fractions: 50 wt % of the composition with the effects of relieving alcoholism and protecting the liver, 20.0 wt % of lactose, 20.0 wt % of corn starch, and 10.0 wt % of talc powder;
wherein by mass fractions, the composition with the effects of relieving alcoholism and protecting the liver comprises 25 parts of chitosan, 30 parts of sodium alginate, 8 parts of gelatin, 3 parts of calcium carbonate and 0.1 parts of gallic acid.

11. The composition according to claim 7, wherein, the preparations are microspheres, the microspheres comprise components of the following mass fractions: 95 wt % of the composition with the effects of relieving alcoholism and protecting the liver, 2.5 wt % of sodium carboxymethylcellulose, and 2.5 wt % of hyaluronic acid;
wherein by mass fractions, the composition with the effects of relieving alcoholism and protecting the liver comprises 25-35 parts of chitosan, 30-50 parts of sodium alginate, 8-15 parts of gelatin, 3-5 parts of calcium carbonate and 0.1-0.3 parts of gallic acid.

12. The composition according to claim 7, wherein, the preparations are microspheres, the microspheres comprise components of the following mass fractions: 80 wt % of the composition with the effects of relieving alcoholism and protecting the liver, 10 wt % of sodium carboxymethylcellulose, and 10 wt % of hyaluronic acid;
wherein by mass fractions, the composition with the effects of relieving alcoholism and protecting the liver comprises 30 parts of chitosan, 40 parts of sodium alginate, 11 parts of gelatin, 4 parts of calcium carbonate and 0.2 parts of gallic acid.

13. A hydrogel tablet for relieving alcoholism and protecting a liver, comprising or prepared from the following components on a basis of weight parts: 20-40 parts of chitosan, 25-55 parts of sodium alginate, 3-20 parts of gelatin, 1-10 parts of calcium carbonate and 0.05-0.5 parts of gallic acid; wherein the hydrogel tablet for relieving alcoholism and protecting the liver comprises a powder particle of chitosan/sodium alginate shell-calcium carbonate core of a core-shell structure encapsulated with a layer of gelatin membrane, wherein a chitosan/sodium alginate forms the shell and the calcium carbonate forms the core, wherein the hydrogel tablet for relieving alcoholism and protecting the liver is prepared by a process including the following steps:
(S1) according to the weight parts, chitosan is added into an acidic solution to prepare a chitosan solution, the resulting chitosan solution is adjusted to pH 5.5~6.0, into which are added the calcium carbonate and the sodium alginate solution in order, treated by vortex vibration and then freeze-dried, to get powder particles of chitosan/sodium alginate shell-calcium carbonate core; the powder particles of chitosan/sodium alginate shell-calcium carbonate core are of a core-shell structure with chitosan/sodium alginate as the shell and with calcium carbonate as the core;
(S2) the gelatin is dissolved in hot water to prepare a gelatin solution, into which is added the gallic acid with stirring to get a gelatin membrane solution; and
(S3) the powder particles of chitosan/sodium alginate shell-calcium carbonate core obtained from S1 are added into the gelatin membrane solution obtained from S2, stirred evenly, freeze-dried, and tableted to get the hydrogel tablet for relieving alcoholism and protecting the liver;
wherein a chronological order of the step S1 and the step S2 is unlimited.

14. The hydrogel tablet for relieving alcoholism and protecting the liver according to claim 13, wherein, a concentration of the chitosan solution is 1%-3%; the concentration of the sodium alginate solution is 0.5%-1.5%; and the concentration of the gelatin solution is 0.5%-1%.

15. The hydrogel tablet for relieving alcoholism and protecting the liver according to claim 13, wherein, a time for the vortex vibration in S1 is 10-20 min.

16. The hydrogel tablet for relieving alcoholism and protecting the liver according to claim 13, wherein, the chitosan solution in S1 is adjusted to pH 5.8.

17. The hydrogel tablet for relieving alcoholism and protecting the liver of claim 13, wherein the calcium carbonate has a particle size of 1000-2500 meshes.

18. A hydrogel tablet for relieving alcoholism and protecting a liver, comprising the following components on the basis of weight parts: 25-35 parts of chitosan, 30-50 parts of sodium alginate, 8-15 parts of gelatin, 3-5 parts of calcium carbonate and 0.1-0.3 parts of gallic acid; wherein the hydrogel tablet for relieving alcoholism and protecting the liver comprises a powder particle of chitosan/sodium alginate shell-calcium carbonate core of a core-shell structure encapsulated with a layer of gelatin membrane, wherein the chitosan/sodium alginate forms the shell and the calcium carbonate forms the core, wherein the hydrogel tablet for relieving alcoholism and protecting the liver is prepared by the process including the following steps:
- (S1) according to the weight parts, chitosan is added into an acidic solution to prepare a chitosan solution, the resulting chitosan solution is adjusted to pH 5.5-6.0, into which are added the calcium carbonate and the sodium alginate solution in order, treated by vortex vibration and then freeze-dried, to get powder particles of chitosan/sodium alginate shell-calcium carbonate core; the powder particles of chitosan/sodium alginate shell-calcium carbonate core are of a core-shell structure with chitosan/sodium alginate as the shell and with calcium carbonate as the core;
- (S2) the gelatin is dissolved in hot water to prepare a gelatin solution, into which is added the gallic acid with stirring to get a gelatin membrane solution; and
- (S3) the powder particles of chitosan/sodium alginate shell-calcium carbonate core obtained from S1 are added into the gelatin membrane solution obtained from S2, stirred evenly, freeze-dried, and tableted to get the hydrogel tablet for relieving alcoholism and protecting the liver;

wherein the chronological order of the step S1 and the step S2 is unlimited.

19. The hydrogel tablet for relieving alcoholism and protecting the liver of claim 18, wherein the tablet comprises 30 parts of chitosan, 40 parts of sodium alginate, 11 parts of gelatin, 4 parts of calcium carbonate and 0.2 parts of gallic acid.

20. The hydrogel tablet for relieving alcoholism and protecting the liver of claim 18, wherein, the gelatin is fish gelatin; the fish gelatin is extracted from leftovers of Tilapia, codfish or Tuna.

* * * * *